(12) United States Patent
Hong

(10) Patent No.: US 7,967,775 B2
(45) Date of Patent: Jun. 28, 2011

(54) IRRIGATION/ASPIRATION TIP

(75) Inventor: Karen Hong, Irvine, CA (US)

(73) Assignee: Alcon, Inc., Hunenburg (CH)

( * ) Notice: Subject to any disclaimer, the term of this patent is extended or adjusted under 35 U.S.C. 154(b) by 465 days.

(21) Appl. No.: 11/621,395

(22) Filed: Jan. 9, 2007

(65) Prior Publication Data

US 2008/0167604 A1   Jul. 10, 2008

(51) Int. Cl.
*A61M 1/00* (2006.01)
(52) U.S. Cl. ................ 604/27; 604/35; 604/43
(58) Field of Classification Search ............ 604/27, 604/30, 33, 35–36, 39–40, 43–44, 93.01, 604/158, 164.01, 164.02, 164.04, 164.07, 604/164.08, 167.01, 167.06, 173, 289, 294
See application file for complete search history.

(56) References Cited

U.S. PATENT DOCUMENTS

| | | | |
|---|---|---|---|
| 1,493,450 A | 5/1924 | Richardson | |
| 3,589,363 A | 6/1971 | Banko et al. | |
| 3,606,878 A | 9/1971 | Kellog | |
| 3,818,913 A | 6/1974 | Wallach | |
| 3,930,505 A | 1/1976 | Wallach | |
| 3,994,297 A | 11/1976 | Kopf | |
| 4,014,333 A * | 3/1977 | McIntyre | 604/43 |
| 4,024,866 A | 5/1977 | Wallach | |
| 4,169,984 A | 10/1979 | Parisi | |
| 4,223,676 A | 9/1980 | Wuchinich | |
| 4,246,902 A | 1/1981 | Martinez | |
| 4,249,899 A | 2/1981 | Davis | |
| 4,265,618 A | 5/1981 | Herskovitz et al. | |
| 4,301,802 A | 11/1981 | Poler | |
| 4,493,694 A | 1/1985 | Wuchinich | |
| 4,515,583 A | 5/1985 | Sorrich | |
| 4,517,977 A | 5/1985 | Frost | |
| 4,570,632 A | 2/1986 | Woods | |
| 4,573,979 A * | 3/1986 | Blake | 604/240 |
| 4,577,629 A | 3/1986 | Martinez | |
| 4,589,414 A | 5/1986 | Yoshida et al. | |
| 4,589,415 A | 5/1986 | Haaga | |
| 4,609,368 A | 9/1986 | Dotson | |
| 4,634,419 A | 1/1987 | Kreizman et al. | |
| 4,634,420 A | 1/1987 | Spinosa | |
| 4,643,717 A * | 2/1987 | Cook et al. | 604/22 |

(Continued)

FOREIGN PATENT DOCUMENTS

EP   0717970 A1   6/1996

(Continued)

OTHER PUBLICATIONS

Fletcher, et al, "Pulsed liquid microjet for microsurgery", Applied Physics Letters, Mar. 26, 2001, 3 pages, vol. 78, No. 13, p. 1933.

*Primary Examiner* — Theodore J Stigell

(57) ABSTRACT

An irrigation/aspiration tip having a relatively rigid cannula attached to a hub and an open end opposite the hub. Coaxially and removable received over the tip is a soft elastomeric or rubber sleeve. The sleeve forms a gap between the sleeve and the cannula, the gap allowing irrigation flow. The distal end of the sleeve is closed by a cap of reduced diameter. The reduced diameter of the cap seals the distal end of the cannula. The relatively soft cap reduces the likelihood that the posterior capsule will tear during cortical clean-up and capsule polishing. Removing the sleeve allows the cannula to be resterilized an unlimited number of times, thereby allowing unlimited reuse of the cannula.

7 Claims, 2 Drawing Sheets

U.S. PATENT DOCUMENTS

| | | | |
|---|---|---|---|
| 4,662,869 A | 5/1987 | Wright | |
| 4,674,502 A | 6/1987 | Imonti | |
| 4,696,298 A | 9/1987 | Higgins et al. | |
| 4,706,669 A | 11/1987 | Schlegal | |
| 4,753,234 A | 6/1988 | Martinez | |
| 4,869,715 A | 9/1989 | Sherburne | |
| 4,897,079 A * | 1/1990 | Zaleski et al. | 604/22 |
| 4,904,238 A * | 2/1990 | Williams | 604/43 |
| 4,909,249 A | 3/1990 | Akkas et al. | |
| 4,909,443 A | 3/1990 | Takagi | |
| 4,911,161 A | 3/1990 | Schechter | |
| 4,922,902 A | 5/1990 | Wuchinich et al. | |
| 4,974,581 A | 12/1990 | Wiksell | |
| 4,986,827 A | 1/1991 | Akkas | |
| 4,989,583 A | 2/1991 | Hood | |
| 4,989,588 A | 2/1991 | Kubota et al. | |
| 5,019,035 A | 5/1991 | Missirlian et al. | |
| 5,019,036 A | 5/1991 | Stahl et al. | |
| 5,084,009 A | 1/1992 | Mackool | |
| 5,106,364 A | 4/1992 | Hayafuji et al. | |
| 5,151,084 A | 9/1992 | Khek | |
| 5,154,694 A | 10/1992 | Kelman | |
| 5,188,589 A | 2/1993 | Wypych et al. | |
| 5,226,910 A | 7/1993 | Kajiyama et al. | |
| 5,250,065 A | 10/1993 | Clement et al. | |
| 5,257,988 A | 11/1993 | L'Esperance, Jr. et al. | |
| 5,261,923 A | 11/1993 | Soares | |
| 5,275,607 A | 1/1994 | Lo et al. | |
| 5,284,472 A | 2/1994 | Sussman et al. | |
| 5,285,795 A | 2/1994 | Ryan et al. | |
| 5,286,256 A | 2/1994 | Mackool | |
| 5,322,504 A | 6/1994 | Doherty et al. | |
| 5,342,293 A | 8/1994 | Zanger | |
| 5,359,996 A | 11/1994 | Hood | |
| 5,380,280 A | 1/1995 | Peterson | |
| 5,413,556 A * | 5/1995 | Whittingham | 604/22 |
| 5,423,330 A | 6/1995 | Lee | |
| 5,505,693 A | 4/1996 | Mackool | |
| 5,554,155 A | 9/1996 | Awh et al. | |
| 5,556,036 A | 9/1996 | Chase | |
| 5,562,692 A | 10/1996 | Bair | |
| 5,591,184 A | 1/1997 | McDonnell | |
| 5,616,120 A | 4/1997 | Andrew et al. | |
| 5,624,392 A | 4/1997 | Saab | |
| 5,624,393 A | 4/1997 | Diamond | |
| 5,634,912 A | 6/1997 | Injev | |
| 5,645,530 A | 7/1997 | Boukhny et al. | |
| 5,653,692 A | 8/1997 | Masterson | |
| 5,669,923 A | 9/1997 | Gordon | |
| 5,674,226 A | 10/1997 | Doherty et al. | |
| 5,685,838 A | 11/1997 | Peters et al. | |
| 5,693,062 A | 12/1997 | Stegmann et al. | |
| 5,718,677 A | 2/1998 | Capetan et al. | |
| 5,766,194 A | 6/1998 | Smith | |
| 5,807,328 A | 9/1998 | Briscoe | |
| 5,865,790 A | 2/1999 | Bair | |
| 5,873,851 A | 2/1999 | Nilsson et al. | |
| 5,879,347 A | 3/1999 | Saadat | |
| 5,885,243 A | 3/1999 | Capetan et al. | |
| 5,891,095 A | 4/1999 | Eggers et al. | |
| 5,947,988 A | 9/1999 | Smith | |
| 6,039,715 A | 3/2000 | Mackool | |
| 6,126,629 A | 10/2000 | Perkins | |
| 6,132,426 A | 10/2000 | Kroll | |
| 6,135,998 A | 10/2000 | Palanker | |
| 6,139,571 A | 10/2000 | Fuller et al. | |
| 6,146,380 A | 11/2000 | Racz et al. | |
| 6,159,175 A | 12/2000 | Strukel et al. | |
| 6,254,587 B1 * | 7/2001 | Christ et al. | 604/521 |
| 6,299,591 B1 | 10/2001 | Banko et al. | |
| 6,340,355 B1 | 1/2002 | Barrett | |
| 6,516,893 B2 | 2/2003 | Pahila | |
| 6,520,929 B2 | 2/2003 | Zaleski | |
| 6,579,270 B2 | 6/2003 | Sussman et al. | |
| 6,871,795 B2 | 3/2005 | Anuskiewicz | |
| 6,902,559 B2 | 6/2005 | Taufig | |
| 6,929,632 B2 | 8/2005 | Nita et al. | |
| 7,014,629 B2 | 3/2006 | Mackool | |
| 2002/0077585 A1 | 6/2002 | Sussman et al. | |
| 2003/0004455 A1 | 1/2003 | Kadziauskas et al. | |
| 2003/0069594 A1 | 4/2003 | Rockley et al. | |
| 2003/0199883 A1 | 10/2003 | Laks | |
| 2003/0208218 A1 | 11/2003 | Kadziauskas | |
| 2004/0068270 A1 | 4/2004 | Allred | |
| 2004/0089080 A1 | 5/2004 | Kadziauskas | |
| 2004/0153093 A1 | 8/2004 | Donovan | |
| 2005/0234473 A1 | 10/2005 | Zacharias | |
| 2005/0277898 A1 | 12/2005 | Dimalanta et al. | |
| 2006/0047241 A1 | 3/2006 | Boukhny | |
| 2006/0212038 A1 | 9/2006 | Boukhny | |
| 2007/0260173 A1 | 11/2007 | Boukhny et al. | |
| 2008/0167604 A1 | 7/2008 | Hong | |

FOREIGN PATENT DOCUMENTS

| | | |
|---|---|---|
| EP | 1199054 A1 | 4/2002 |
| EP | 1310267 A2 | 5/2003 |
| EP | 1310267 A3 | 5/2003 |
| EP | 1199054 B1 | 5/2004 |
| EP | 1607076 A1 | 12/2005 |
| EP | 1310267 B1 | 1/2008 |
| EP | 1943990 A1 | 7/2008 |
| WO | WO 92/18049 A1 | 10/1992 |
| WO | WO 96/24314 A1 | 8/1996 |

* cited by examiner

IRRIGATION/ASPIRATION TIP

This invention relates to aspiration tips and more particularly to aspiration tips used in ophthalmic phacoemulsification surgery.

BACKGROUND OF THE INVENTION

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial lens.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by the artificial lens.

Prior to the introduction of the artificial intraocular lens into the eye, softer cortical material is aspirated from the eye using an aspiration tip. Aspiration tips are similar to phacoemulsification tips, but with a smaller opening at the distal end and not typically vibrated ultrasonically. The aspiration tip may also be used to "polish" the posterior capsule to remove residual epithelial cells and reduce the risk of posterior capsule opacification. Conventional aspiration tips are made from titanium or stainless steel. These tips must be highly polished to reduce burrs and eliminate sharp edges that may snag or tear the posterior capsule. Polishing the aspiration port and the interior lumen of the aspiration tip, however, is very difficult and some burrs may remain even after extensive polishing. During capsule polishing and cortical clean-up, the posterior capsule may be drawn partially into the aspiration port and interior lumen of the aspiration tip. If these portions of the aspiration tip contain rough edges or burrs, tearing of the posterior capsule can occur. In addition, during repeated use, the exterior of the aspiration tip can develop burrs and rough spots that can snag or tear the capsule.

One prior aspiration tip, disclosed in U.S. Pat. No. 5,718,677 (Capetan, et al.) overcomes the problems associated with metal tips by installing a silicone rubber tip cap over the distal end of the metal cannula. While the device is effective is reducing or eliminating some of the risks discussed above, the rubber tip cap must be fixed to the metal tip to prevent the tip cap from sliding off of the metal tip. While the rubber tip cap is sterilizable in an autoclave, the tip cap is much more easily damaged than the metal cannula, thereby limiting the number of reuses of the tip assembly. In addition, as with other commercially available tips, the tip cap does not provide any irrigation function, so a separate irrigation handpiece or an infusion sleeve over the aspiration tip must be used.

Accordingly, a need continues to exist for an irrigation/aspiration tip that reduces the possibility of tearing the posterior capsule during cortical clean-up and capsule polishing.

BRIEF SUMMARY OF THE PREFERRED EMBODIMENT

The present invention improves upon prior art aspiration tips by providing an irrigation/aspiration tip having a relatively rigid cannula attached to a hub and an open end opposite the hub. Coaxially and removably received over the tip is a soft elastomeric or rubber sleeve. The sleeve forms a gap between the sleeve and the cannula, the gap allowing irrigation flow. The distal end of the sleeve is closed by a cap of reduced diameter. The reduced diameter of the cap seals the distal end of the cannula. The relatively soft cap reduces the likelihood that the posterior capsule will tear during cortical clean-up and capsule polishing. Removing the sleeve allows the cannula to be resterilized an unlimited number of times, thereby allowing unlimited reuse of the cannula.

One objective of the present invention is to provide an irrigation/aspiration tip that reduces the likelihood of tearing the posterior capsule.

Another objective of the present invention is to provide an aspiration tip having an open lumen sealed with a flexible cap.

Other objectives, features and advantages of the present invention will become apparent with reference to the drawings, and the following description of the drawings and claims.

DETAILED DESCRIPTION OF THE PREFERRED EMBODIMENTS

Figure 1:
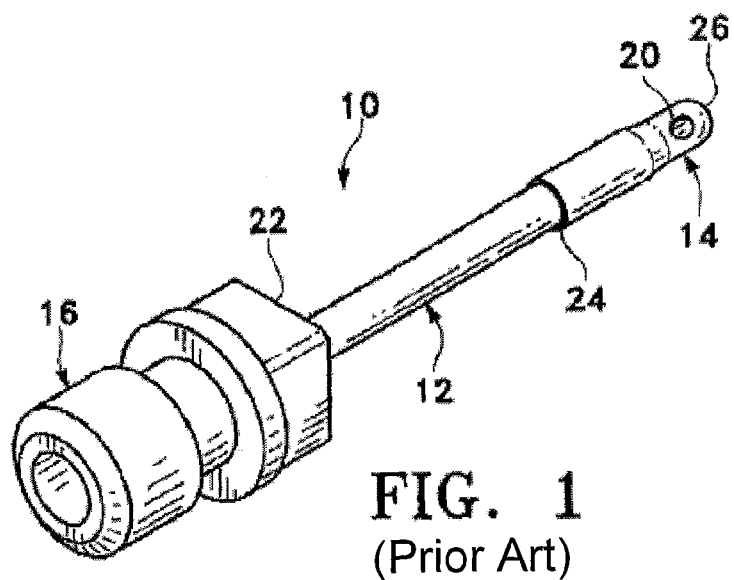
FIG. 1 is an expanded perspective view of a prior art aspiration tip.

As best seen in FIG. 1, prior art aspiration tip 10 consists of aspiration cannula 12 and cap 14. Cannula 12 is open at distal end and is attached to hub 16 at proximal end 22. Hub 16 allows aspiration tip 10 to be attached to an appropriate handpiece (not shown). Distal end is sealed by cap 14. Cap 14 is generally tubular in shape, is open on proximal end 24 and closed on distal end 26 except for port 20.

Figure 2:
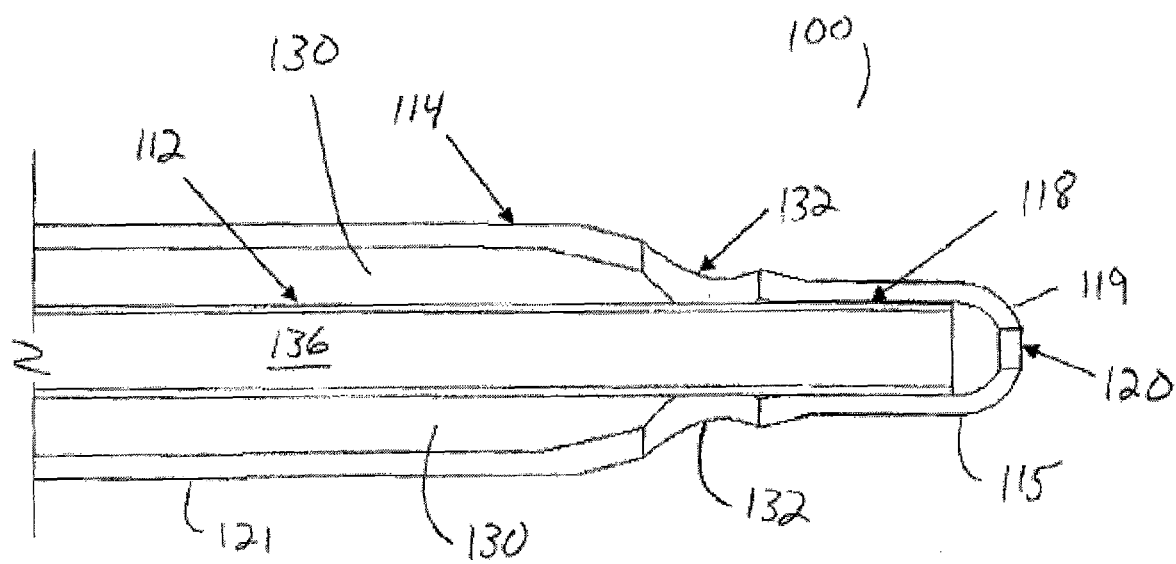
FIG. 2 is an enlarged cross-sectional view of the irrigation/aspiration tip of the present invention.
Figure 3:
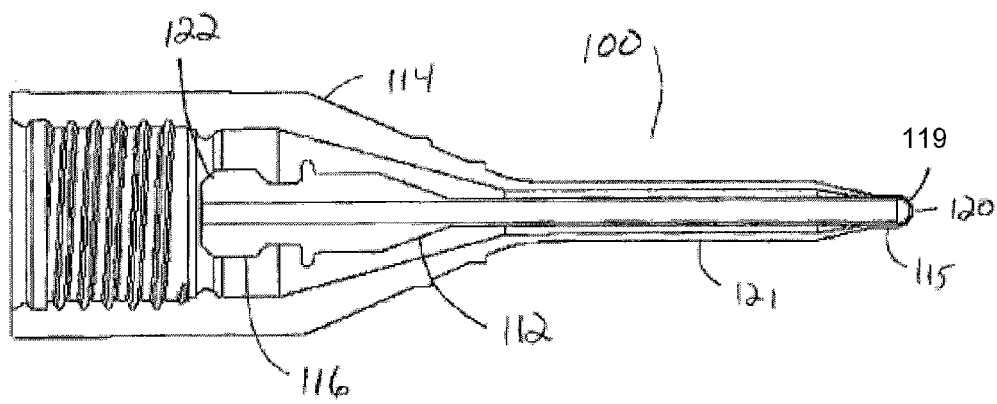
FIG. 3 is an enlarged cross-sectional view of the irrigation/aspiration tip of the present invention.
Figure 4:
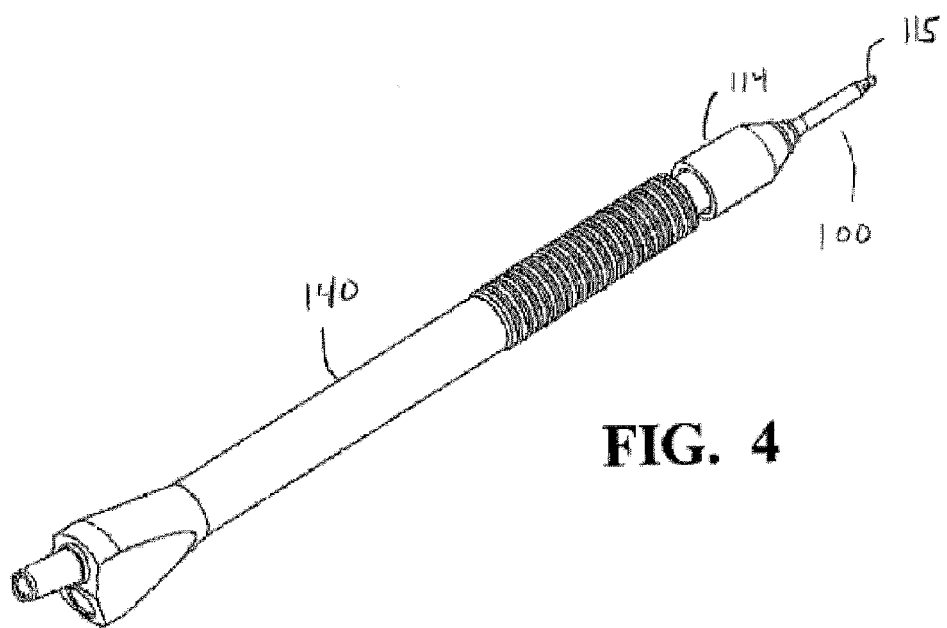
FIG. 4 is an enlarged perspective view of the irrigation/aspiration tip of the present invention installed on a handpiece.

As best seen in FIGS. 2, 3 and 4, irrigation aspiration tip 100 of the present invention generally includes aspiration cannula 112 and sleeve 114. Cannula 112 is open at distal end 118 and is attached to hub 116 at proximal end 122. Hub 116 allows aspiration tip 100 to be attached to handpiece 140. Distal end 118 of cannula 112 is sealed by reduced diameter end cap 115, which is integrally formed at distal end 119 of shaft 121 of sleeve 114. End cap 115 is generally tubular in shape and closed on its distal end except for port 120. The reduced diameter of end cap 115 causes end cap 115 to seal tightly about distal end 118 of cannula 112. Sleeve 114 forms coaxial gap 130 around cannula 112. Gap 130 allows irrigation flow down gap 130 and out ports 132. When vacuum is applied to interior lumen 136 of cannula 112, material can be aspirated through port 120, down interior lumen 136 and out of tip 110.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An irrigation/aspiration tip, comprising:
   a) an open aspiration cannula, the cannula having a hub enabling attachment of the cannula to a handpiece and an open end opposite the hub; and
   b) a removable, elastomeric sleeve, the sleeve coaxially surrounding the cannula and having a shaft, the shaft having an end cap of reduced diameter, the end cap sealing about the open end of the cannula;
   wherein the sleeve is coupled to the cannula through a friction-fit between a portion of the end cap and the cannula and wherein the portion of the end cap forming the friction-fit with the cannula is between an aspiration port defined by the sleeve and an irrigation port defined by the sleeve;
   wherein a proximal portion of the elastomeric sleeve includes internal threads;
   wherein the end cap defines the aspiration port and wherein the aspiration port is axially aligned with the open end of the cannula opposite the hub;
   wherein the aspiration port is located at a distal tip of a rounded outer end of the end cap, the aspiration port located distal to the open end of the cannula.

2. The irrigation/aspiration tip of claim 1, wherein the aspiration cannula is configured to be repeatedly reused by sterilizing the aspiration cannula after removal of the elastomeric sleeve.

3. The irrigation/aspiration tip of claim 1, wherein the sleeve is external to the hub and hand piece.

4. The irrigation/aspiration tip of claim 3, further comprising a gap between a proximal end surface of the sleeve and the hand piece.

5. An irrigation/aspiration tip, comprising:
   a rigid, open aspiration cannula, the cannula having a hub enabling attachment of the cannula to a handpiece and an open end opposite the hub; and
   a removable, elastomeric sleeve, the sleeve coaxially surrounding the cannula and having a shaft, the shaft having an end cap of reduced diameter, the end cap sealing about the open end of the cannula;
   wherein the aspiration cannula is configured to be repeatedly reused by sterilizing the aspiration cannula after removal of the elastomeric sleeve and replacing the elastomeric sleeve after sterilizing the aspiration cannula;
   wherein the end cap defines an aspiration port located at a distal tip of a rounded outer end of the end cap; and
   wherein the aspiration port is axially aligned with the open end of the cannula opposite the hub, the aspiration port located distal to the open end of the cannula;
   wherein a proximal portion of the elastomeric sleeve includes internal threads;
   wherein the sleeve is configured to leave a gap between a proximal end surface of the sleeve and a grip portion of the handpiece when the sleeve is fully screwed onto the handpiece.

6. The irrigation/aspiration tip of claim 5, wherein the sleeve is a rubber material.

7. The irrigation/aspiration tip of claim 5, wherein the sleeve is coupled to the cannula through a friction-fit between a portion of the end cap and the cannula and wherein the portion of the end cap forming the friction-fit with the cannula is between the aspiration port defined by the sleeve and an irrigation port defined by the sleeve.

* * * * *